United States Patent [19]
Bailey et al.

[11] Patent Number: 5,611,994
[45] Date of Patent: Mar. 18, 1997

[54] LUMINOMETER

[75] Inventors: James S. Bailey, Arlington; Phillip P. Brown, Centreville; Kenneth W. Simpson, Marshall; Walter W. Taylor, Dale City, all of Va.

[73] Assignee: Dynatech Laboratories, Inc., Chantilly, Va.

[21] Appl. No.: 561,755

[22] Filed: Nov. 22, 1995

[51] Int. Cl.⁶ .................................................. G01N 21/76
[52] U.S. Cl. .......................... 422/52; 422/107; 422/82.05; 250/361 C
[58] Field of Search .......................... 422/52, 107, 82.05, 422/82.08; 250/361 R, 361 C

[56]  References Cited

U.S. PATENT DOCUMENTS

| | | | |
|---|---|---|---|
| 3,520,660 | 7/1970 | Webb | 422/52 |
| 4,772,453 | 9/1988 | Lisenbee . | |
| 4,985,631 | 1/1991 | Wannlund et al. | 250/361 R |
| 5,082,628 | 1/1992 | Andreotti et al. . | |
| 5,202,091 | 4/1993 | Lisenbee . | |
| 5,290,513 | 3/1994 | Berthold et al. . | |
| 5,340,747 | 8/1994 | Eden | 436/172 |

Primary Examiner—Jeffrey Snay
Attorney, Agent, or Firm—Donald C. Casey, Esq.

[57]  ABSTRACT

An improved luminometer is provided which uses a top loading plate carrier which receives a microtitration plate and uses a mask having an aperture corresponding to each test cell in the plate carrier. When the mask rotates downwardly to cover the microtitration plate, the plate carrier automatically orients the microtitration plate in the X, Y and Z directions. Reagents are added to the individual test cells through the mask aperture. Each reagent injector is extendable and retractable so that liquids can be added below the mask aperture during purging or washing and then the injector retracted. A pump is provided for each injector which is driven by a stepper motor and a rack and pinion connection to a syringe.

17 Claims, 8 Drawing Sheets

LUMINOMETER

FIELD OF THE INVENTION

This invention relates to a measuring device used for measuring the intensity of light generated in a test cell and, in particular, to an improved luminometer which reliably and efficiently processes test samples to accurately record the intensity of the luminescent reaction in individual test cells.

Description of the Prior Art

Luminometers have been known for many years and examples of such devices are described, for example, in U.S. Pat. Nos. 4,772,453; 5,082,628; 5,202,091; and 5,290,513.

Biological samples may be analyzed using fluorometry or such samples may be analyzed based on luminescence. In fluorometry, reagents are added to a test cell and a light beam is either passed through the cell or into the cell and reflected upwardly through the open top of the cell. In either instance, the intensity of the light beam is proportional to a characteristic of the reaction in the test cell. In fluorometry, if the light beam is passed downwardly and the intensity recorded below the cell, the native fluorescence of the material used to construct the window in the bottom of the cell can introduce air into the reading. In the event it is desired to use a frontal approach type of fluorometer, a light beam is passed downwardly into the cell and then reflected upwardly. This creates an optical problem in isolating the reflected light for an intensity reading.

In luminometry, however, reagents are added to a test cell and a luminescent reaction results wherein light is generated either biologically or chemically, and the intensity of the light generated in the test cell is proportional to a characteristic to be measured. In this instance, the light generated in the cell may be measured either above the open top of the cell or, if the cell contains a transparent window, below the bottom thereof. Luminescent reactions are typically much more accurate than fluorescent reactions, and require much small quantities of reagents.

Fluorometers and luminometers typically can utilize a single test cell, a strip of test cells, or, in many instances, a plate of test cells typically having eight rows of twelve cells each. Such a microtitration plate is manufactured by the assignee of this invention, Dynatech Laboratories, Inc., under the trademark MICROTITER. The MICROTITER plates are formulated of plastic material and may be pigmented either black to minimize crosstalk between adjacent cells or white in order to increase the reflected signal from within the cell.

As will be obvious to those skilled in the art, when MICROTITER plates are used in laboratory analysis, it is necessary to process a large number of samples in a short period of time to accurately and efficiently evaluate the reactions.

In a luminometer, it is necessary to eliminate both crosstalk between adjacent cells and any influence of ambient light on the reading. Crosstalk can be minimized by using black MICROTITER plates and by reading the reflected luminescence through the open cell top rather than through the bottom of the cell. Because the optical system is disposed above the open cell top, however, it is necessary to ensure that reagents added to the cell do not splatter upwardly onto the lens or other optical components. It is further necessary to provide against jostling, spilling, or the like of the contents of the cell as the plate is handled. In some fluorometers and luminometers, a conveyor system moves from one side of the unit to another wherein MICROTITER plates are admitted at one side of the machine, treated, read and expelled from the opposite side. While such side loading machines are well known, they have disadvantages, both from the standpoint of the amount of floor space required and the difficulty in sealing the interior against the admission of ambient light.

SUMMARY OF THE INVENTION

It has been discovered that an improved luminometer can be provided in which individual trays or MICROTITER plates are top loaded onto a plate carrier tray which is then retracted into the machine interior so that it can be sealed against the admission of ambient light. A mask is provided over the tray, and the tray is oriented both in the X and Y directions, and is levelled in the Z direction. The plate carrier of this invention then is intended to orient and stabilize the tray during the admission of reagents and reading of the luminescent reaction in each cell.

In addition to an improved plate carrier, it has been discovered that the optical system can be protected against splattering and the like by providing that each injector wherein reagents are injected into the cell is extendable and retractable. Therefore, when the injector is purged or washed, it may be extended through the mask so that the liquid used is directed against the side of a cell and then retracted automatically so that a reagent may be used on a test cell. The optical system of this invention then utilizes a columnating lens disposed above the cell to direct a beam of light upwardly against a mirror which reflects the light onto the light sensitive surface of a photo multiplier tube (PMT) where a reading is taken. A calibration system is built in to calibrate the PMT so that the PMT can be calibrated repeatedly during use without substantial down time.

The injectors used also are provided with a syringe pump for each injector wherein a stepper motor is used to inject the liquid reagent into the cannula for deposition into a test cell.

Accordingly, is an object of this invention to provide an improved luminometer having a top loading capability wherein MICROTITER trays may be inserted into the machine individually whereupon they are oriented in the X and Y direction, and levelled in the Z direction, and reagents are added individually to the cells and the luminescent reaction taken.

It is another object of this invention to provide a luminometer wherein when the injector is to be purged or washed, liquids passing therethrough may be directed against the side of the individual MICROTITER cell to avoid splattering.

It is still another object of this invention to provide an efficient pumping system wherein a stepper motor operates a rack and pinion to inject from a syringe predetermined quantities of reagents into the individual injectors for deposition into the individual test cells in the MICROTITER plate.

These and other objects will become readily apparent with reference to the drawings and following description wherein:

DETAILED DESCRIPTION OF THE INVENTION

Figure 1:
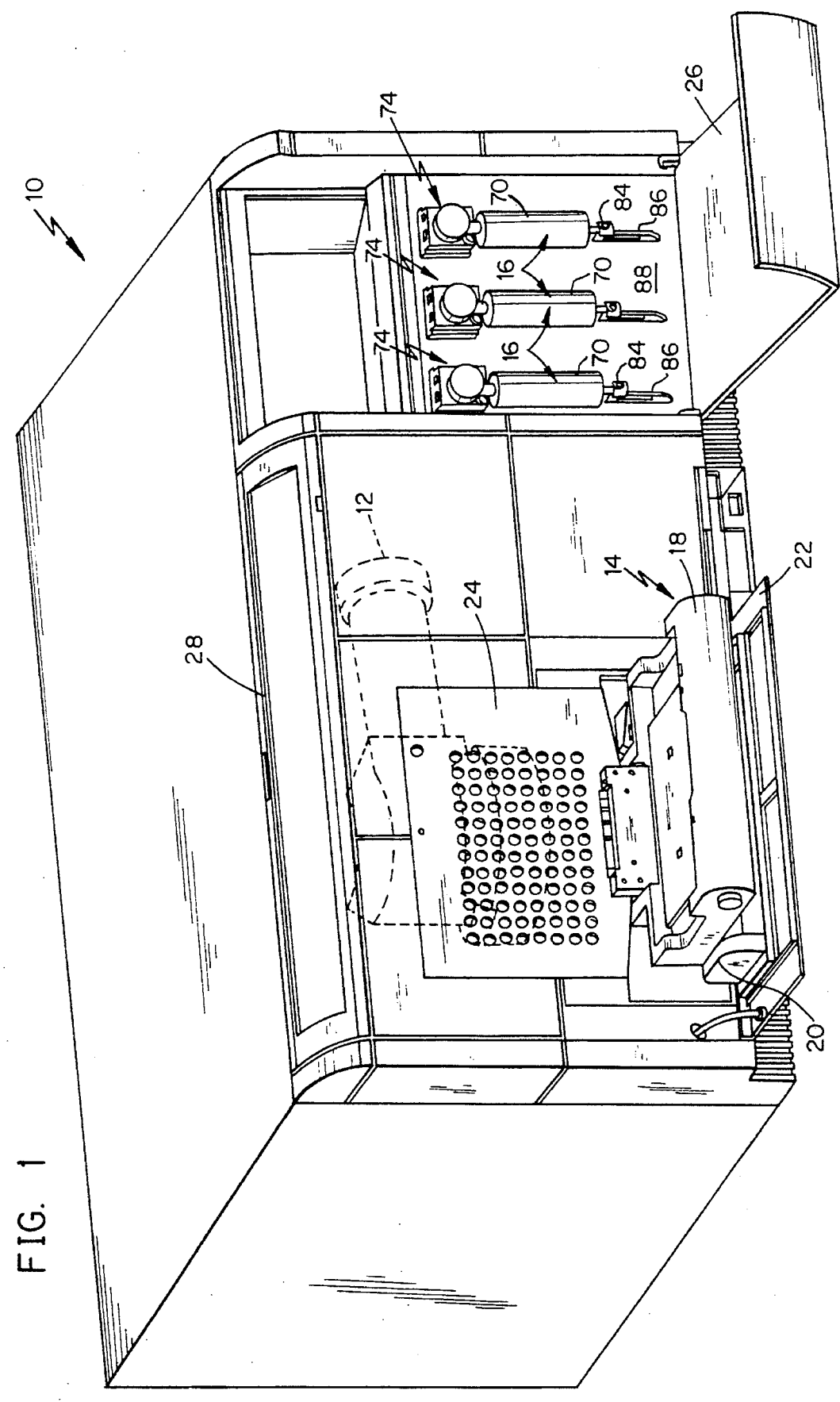
FIG. 1 is a perspective view of the front of the luminometer of this invention showing the optical system in phantom.

With attention to the drawing and to FIG. 1 in particular, the luminometer 10 of this invention includes an optical system 12, a top loading plate carrier 14 and, in this instance, three syringe pumps 16 are used, as will be subsequently described, in connection with dispensing reagents.

The plate carrier 14 includes a retractable base 18 which is slidably mounted on a frame 20 and supported by a door 22 so that the plate carrier 14 can be moved into the interior of luminometer 10 and door 22 closed to exclude ambient light whereupon the mask 24 will be rotated to the down position, and the optical system 12 will be centered over the mask 24, as will be subsequently described. A second door 26 normally encloses syringe pumps 16. A display may also be provided at plate 28.

Figure 2:
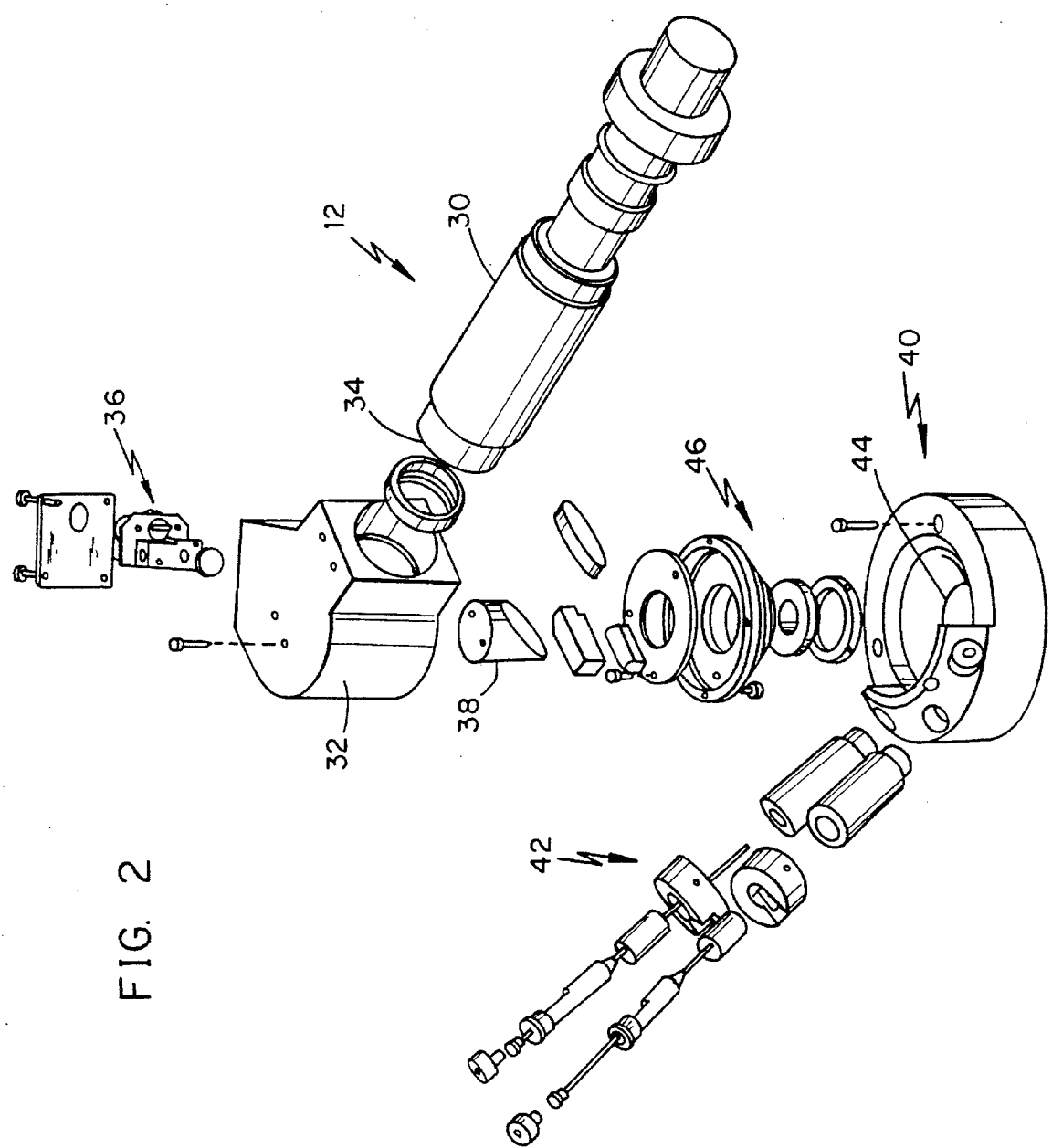
FIG. 2 is an exploded view of the optical system and injectors.

With attention to FIG. 2, the optical system 12 includes photo multiplier tube 30 which is mounted in a block 32 with a light sensitive face 34 disposed within a chamber in block 32. The calibration device 36 is also mounted on block 32. The calibration device is described in a copending patent application filed on even date herewith and assigned to the owner of this invention. Accordingly, this patent application entitled "CALIBRATION SYSTEM FOR A PHOTO MULTIPLIER TUBE", Walter W. Taylor, inventor, is hereby incorporated by reference in its entirety herein.

A mirror 38 is provided within block 32 to direct light onto the light sensitive face 34 of the photo multiplier tube 30. A collar 40 is provided for mounting the injectors 42 and, typically, three injectors are provided. As will be subsequently described, the test well is directly centered below the aperture 44 in collar 40. A lens system 46 is provided within collar 40. Lens system 46 includes a columnating lens. Light then from the test cell shines upwardly through aperture 44 and is columnated by the lens in system 46. The column then is directed upwardly against the angled surface of mirror 38. Mirror 38 then directs the column of light onto the light sensitive surface 34 of the PMT 30. The associated software and microprocessors are not shown. The calibrated PMT reading then is proportional to the intensity of the light generated by the reaction in the test cell and, therefore, is proportional to the characteristic of the test sample to be measured.

Figure 3:
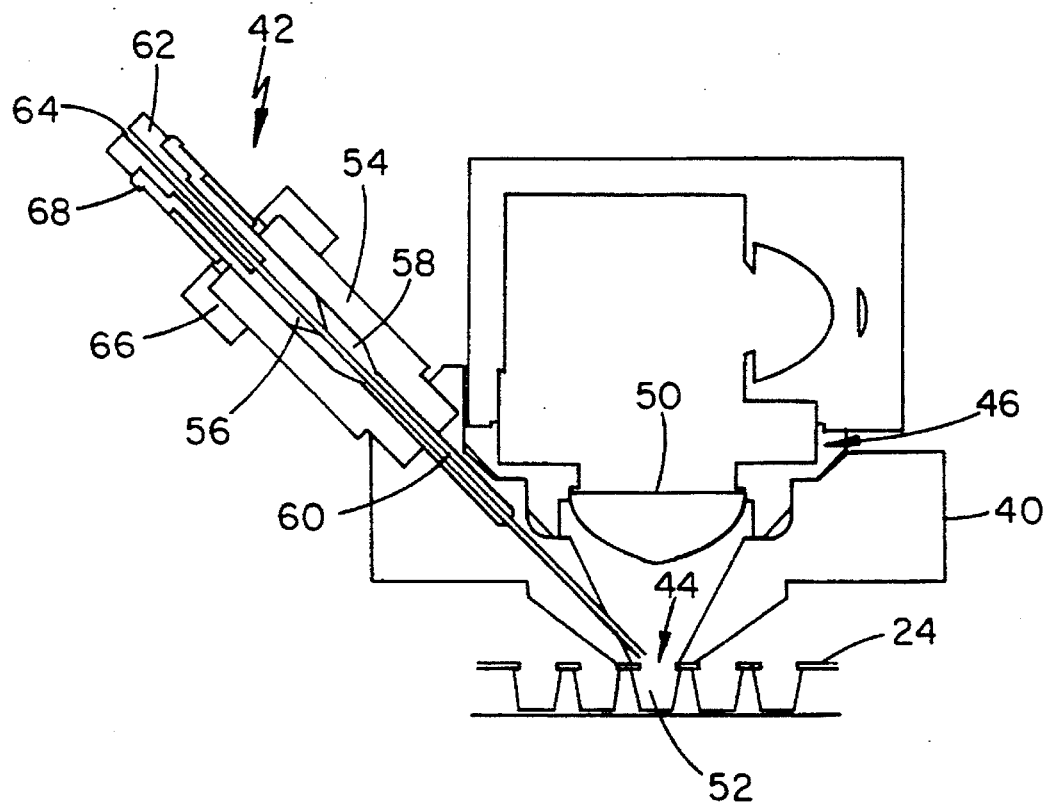
FIG. 3 is a schematic view in partial cross section of a retracted injector of this invention.
Figure 4:
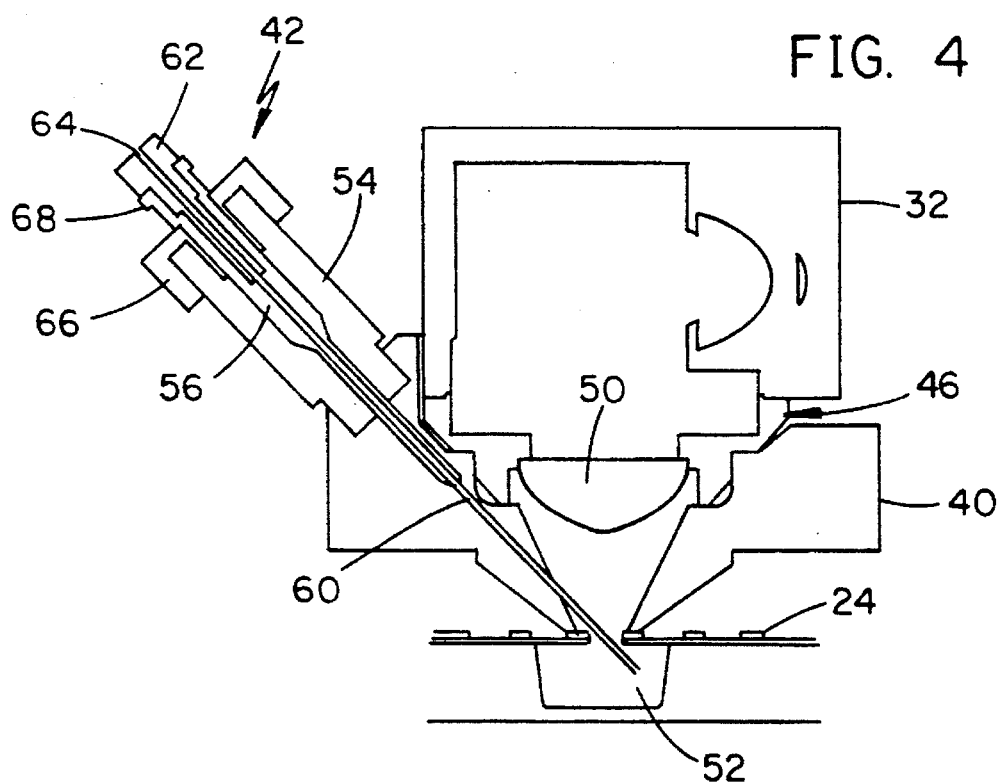
FIG. 4 is a view similar to FIG. 3 wherein the injector is extended.

With attention to FIGS. 3 and 4, the lens system 46 and the columnating lens 50 therefor are disposed above an individual test cell 52 as shown. In FIG. 3, the injector 42 is shown in a retracted position. Injector 42 includes a solenoid 54 which houses a piston 56 within a cavity 58. A cannula 60 extends the length thereof and is affixed to a cap 62 which in turn is snap-fitted within piston 56. A conduit, not shown, is intended to extend from opening 64 in cap 62 whereby a reagent from the pump system, as will be subsequently explained, flows through cannula 60 to the test cell 52. A plunger stop 66 is provided on solenoid 54 and a spring (not shown) extends from the rim 68 of piston 56 to the plunger stop 66. When solenoid 54 is activated, the piston 56 then slides from the position of FIG. 3 to the position of FIG. 4 whereby the cannula extends downwardly through the mask 24 and into the test cell 52. When the solenoid 54 is deactivated, the spring urges the piston outwardly from the position shown in FIG. 4 to the position shown in FIG. 3 thereby withdrawing the cannula through aperture 44. In this way, when liquid is passed through the cannula 60 to purge or wash it, there will be no splattering which could reach lens 50 or associated equipment.

In addition, because cap 62 is snap-fitted within piston 56, using, for example, a conventional O-ring or the like, the cap 62 and cannula 60 with the associated conduit (not shown) which is mounted at opening 64 can be withdrawn from piston 56 without disconnecting the liquid supply through opening 64. The cannula 60 can then be cleaned, replaced, or the like, and reinserted into piston 56 quickly and efficiently.

Figure 5:
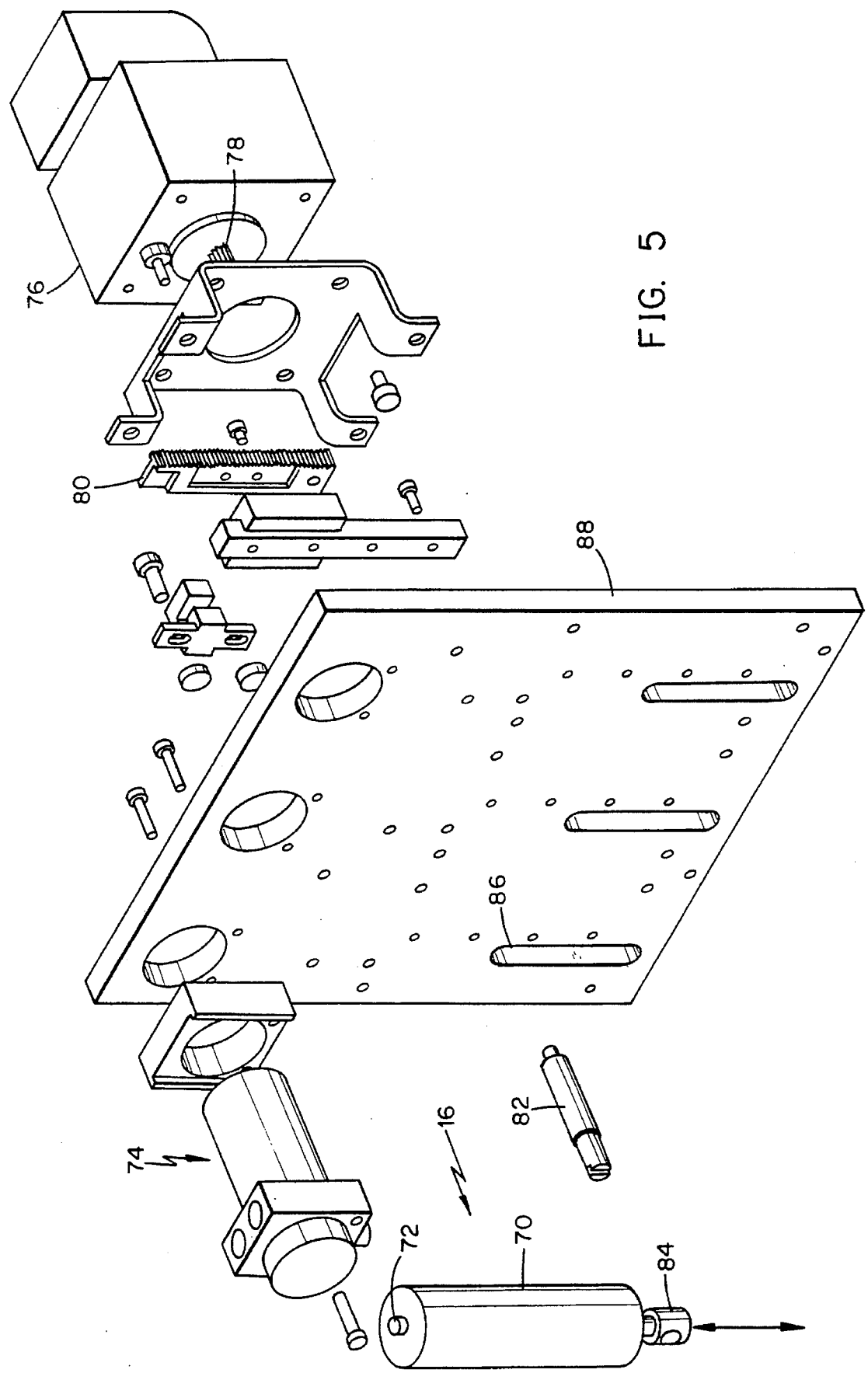
FIG. 5 is an exploded view of a syringe pump of this invention used for dispensing reagents to the injectors.
Figure 6:
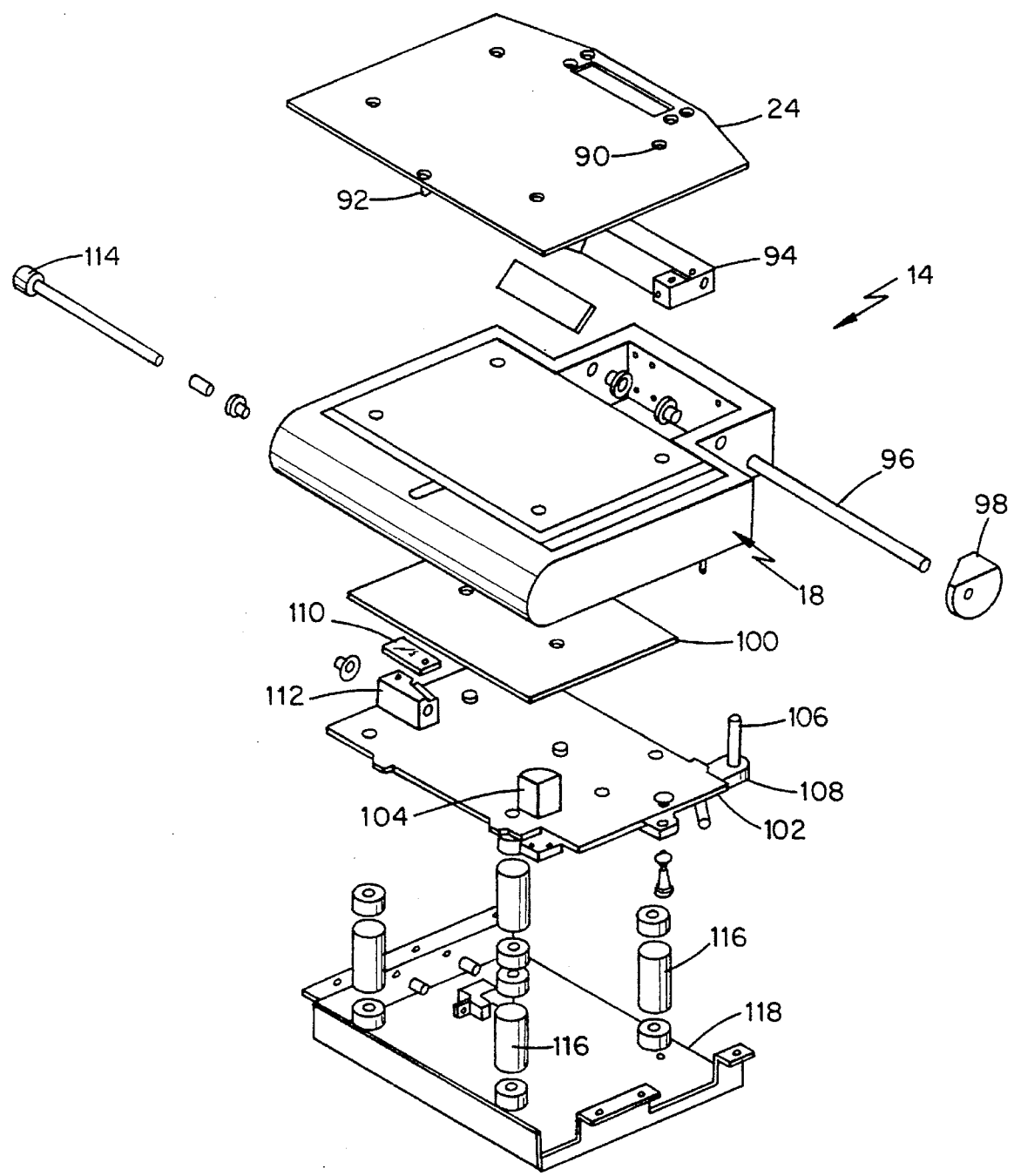
FIG. 6 is an exploded view of the plate carrier of this invention.

With reference to FIGS. 1 and 5, the liquid supply to injectors 42 uses a syringe pump 16 for each injector 42. The syringe pump 16 includes a syringe 70 which is conventional and is a reservoir for the reagent used. The outlet 72 flows through a block and valve 74 and is expelled into a conduit (not shown) which connects with cap 62 at opening 64.

Each syringe 70 is driven by a stepper motor 76 which has an output shaft 78 which constitutes the pinion on a rack 80. Rack 80 is coupled to a connecting link 82 which, in turn, is affixed to a syringe piston 84. The link 82 extends through an associated slot 86 in a mounting plate 88. Rotational motion then of the output shaft 78 of the motor, will drive the rack which, in turn, will translate upward movement of the rack to upward movement of the piston 84 thereby expelling liquid from syringe 70 into valve 74 and the associated conduit. It has been discovered that a simple rack and pinion connection between the motor 76 and the syringe 70 will be sufficient to dispense the small quantities of reagents used in the test cells.

Figure 7:
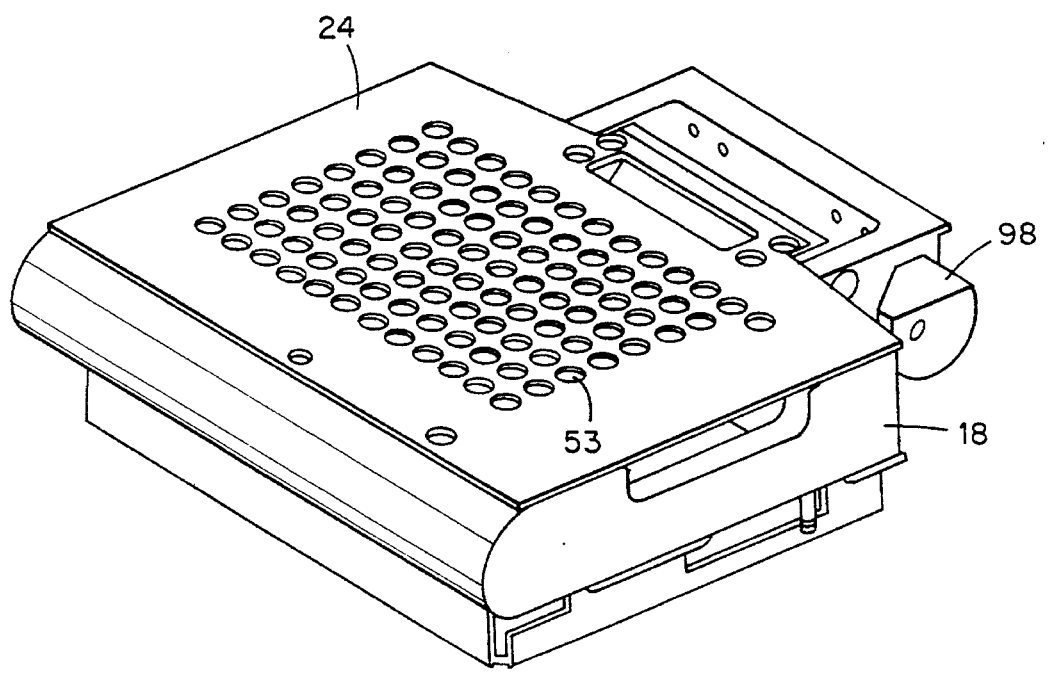
FIG. 7 is a view of a plate carrier of this invention with the mask in a closed position.

With attention to FIG. 6–11, the plate carrier 14 of this invention as described above includes a base 18 and the mask 24 which has an aperture 90 for each test cell, and which further mounts a latch pin 92 as will be subsequently described. The mask 24 is attached by a mask mount 94 to a shaft 96 which extends through base 18 so that movement of the mask from a close position, as shown in FIG. 7, to an open position as shown in FIG. 9, will cause the shaft 96 to rotate. A cam 98 is provided on shaft 96. A conventional heater plate 100 is provided within housing 18 and this heater is mounted on an elevator plate 102. Plate 102 further mounts a biased lever 108 which in turn mounts a plate pusher element 104 and a cam follower 106. In addition, a latch 110 and mount 112 are provided. Latch 110 receives pin 92 and the latch release mechanism 114, as will be subsequently described. Elevator 102 is then mounted on spring loaded pistons 116 located one at each corner for levelling the elevator, and the spring loaded pistons 116 are, in turn, mounted on a base plate 118.

Figure 11:
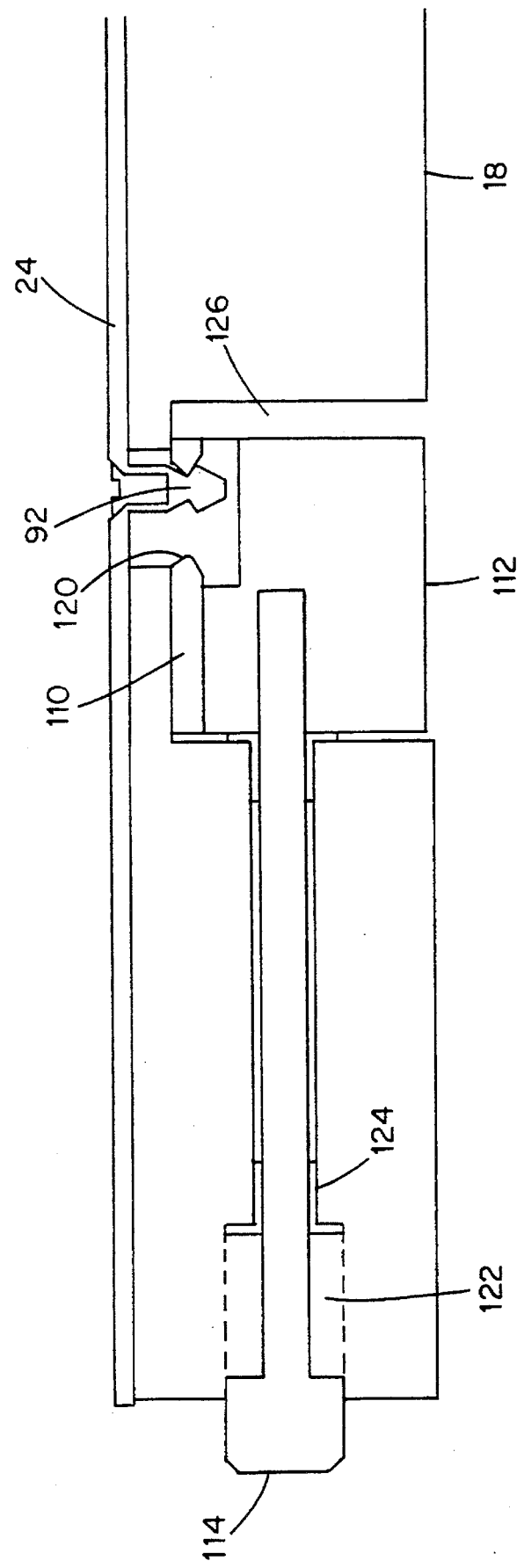
FIG. 11 is a schematic fragmentary view of the latch mechanism for the plate carrier of this invention.

With attention to FIG. 11, the latch pin 92 mounted on mask 24 has a circumferential groove which normally is received in a corresponding angled opening 120 in latch 110. A pin 114 is provided for releasing the latch mechanism which is biased by a spring (not shown) located in chamber 122 and a bearing 124 may also be provided. Depression of pin 114 laterally then moves latch mount 112 within the chamber 126 in the plate carrier base 18 whereby the latch 110 releases pin 92. As will be obvious to those skilled in the art, the pin 114 is normally urged outwardly to maintain the latch pin in the angled opening 120. This spring action must be strong enough to keep the mask latched to the housing 18 against the action of leveller springs 116.

With attention to FIGS. 7–10, when a MICROTITER plate 136 is placed on elevator 100, there is a provision for X-Y orientation thereof within the plate holder 14 as follows:

Lever 108 extends from a pivotal mount 134 in the center thereof wherein the angled plate mover 104 is mounted at one end, and the cam follower 106 at an opposite end. When cam 98 rotates as shaft 96 is rotated, the lever 108 moves about its pivot point 134. A spring is located at portion 130 of lever 108 so that lever 108 is normally urged into the position shown in FIG. 8.

Figure 8:
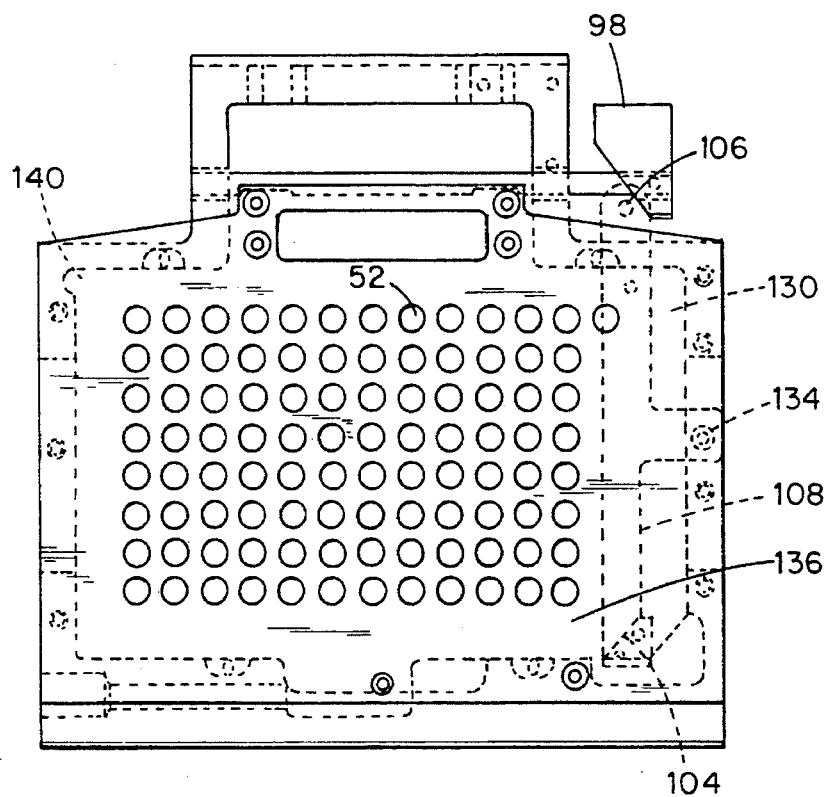
FIG. 8 is a plan view similar to FIG. 7.
Figure 9:
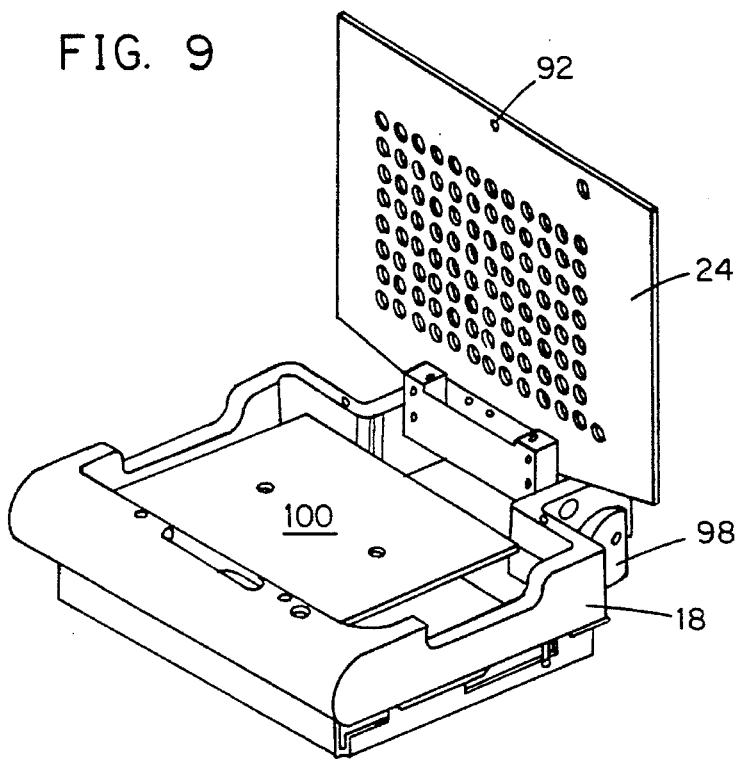
FIG. 9 is a view in perspective of the plate carrier of this invention with the mask rotated to the "up" position.

As shown in FIG. 8, when the MICROTITER tray 136 is disposed within the plate holder 14, it is urged into a datum corner 140 by plate pusher 104 so that the MICROTITER plate 136 will always be oriented with each test cell 52 disposed below corresponding aperture 53 in mask 24.

Figure 10:
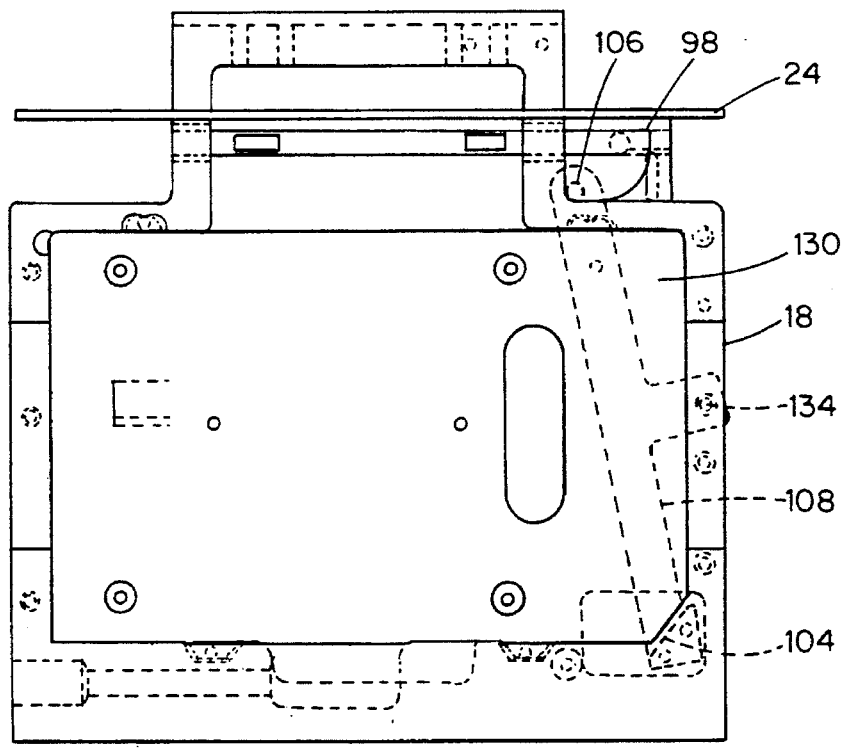
FIG. 10 is a plan view of the plate carrier of FIG. 9.

When the mask is rotated from the position shown in FIGS. 7 and 8 to the position shown in FIGS. 9 and 10, the cam 98 will rotate against follower 106 to move plate pusher 104 into the position shown in FIG. 10 whereby the MICROTITER plate can be manually removed from the heater plate 100. Furthermore, the MICROTITER plate is intended to be urged downwardly by the closing of the mask 24 from the position shown in FIG. 9 to the position shown in FIG. 7. This then will cause the leveller piston springs 116 to urge the tray 136 upwardly against the undersurface of mask 24. In this way then, the MICROTITER tray, when inserted in the plate carrier 14, will be oriented in the X, Y and Z directions by the closure of the mask alone from the position shown in FIG. 9 to the position shown in FIG. 7. In the closed position then, the plate carrier can be slidably moved into the interior of housing 10, door 22 can be closed, and the optical system 12 will then be aligned with the datum corner 140. An automatic X-Y movement of the plate carrier then relative to the fixed optical system 12 will achieve the dispensing of reagents into each cell, and the reading thereof. As will be obvious to those skilled in the art, this invention is not intended to be limited to means for achieving the readings or the relative movement between the microtitration tray and the optical system.

In summary then, the luminometer of this invention utilizes a top loading plate carrier for microtitration plates which are manually inserted therein, and are automatically oriented in the X, Y and Z directions by closure of a mask downwardly over the plate whereby the individual apertures in the mask are aligned with the test cells in the microtitration plate. The plate carrier is then slidably moved into the machine and a door closed to seal off ambient light.

The optical system in the device of this invention is attached to a collar of dispensers which are, in turn, extendable and retractable. Reagents are added to each individual cell by the injector through the aperture in the mask. Movement of the injector is achieved through the action of a solenoid and a pistons wherein the piston is biased to return from the extended position to the retracted position after the purging or washing actions are completed. The optical system of this invention then uses light which shines upwardly through the open top of the test cell and is columnated by a lens whereupon the column shines upwardly against a mirror which diverts the column of light against the surface of a PMT for reading of the intensity thereof. A calibration system is further provided to continually calibrate the PMT to ensure accuracy of the readings.

As will be obvious to those skilled in the art, this invention is not intended to be limited to the particular microprocessors or software used within the scope of the instant description. It will be obvious to those skilled in the art that appropriate microprocessor controls are provided to facilitate use of the luminometer of this invention to rapidly and efficiently process test samples in microtitration plates or the like.

It will be readily seen by one of ordinary skill in the art that the present invention fulfills all of the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

We claim:

1. In a luminometer having at least one injector for injecting a reagent into a sample containing open top test cell to produce a luminescent reaction and an optical system for reading the intensity of the light generated in said test cell by said reaction, the improvement comprising:

a top loading holder for said test cell having upstanding walls, a base and an open top;

a mask having at least one aperture therein, hingedly attached at an edge thereof to an upper wall portion of said holder and rotatable between an open position and a closed position wherein said mask overlies the open top of said holder, means carried by said holder for receiving said test cell and orienting the same so that the open top of said test cell is in registration with the aperture in said mask, responsive to rotational movement of said mask from an open position to a closed position.

2. The luminometer of claim 1 wherein a plurality of test cells are provided in a plate and said mask has a like number of apertures therein.

3. The luminometer of claim 2 wherein said plate is rectangular.

4. The luminometer of claim 3 wherein said means for orienting includes means for orienting said plate within said holder in the X, Y, and Z directions responsive to rotational movement of said mask.

5. The luminometer of claim 4 wherein the base of said holder includes a flat plate member adapted to receive said test cell plate and vertical bias means normally urging said plate upwardly.

6. The luminometer of claim 5 further comprising cam means carried by said base and horizontally biased lever means disposed within said base including follower means on said lever means for orienting said test cell plate in the X and Y directions.

7. The luminometer of claim 6 wherein when said mask is in the closed position the under surface thereof abuts said test cell plate and said mask urges said plate downwardly against said vertical bias means.

8. The luminometer of claim 7 further comprising a hinge interconnecting an edge of said mask and a wall portion of said base, said hinge including a shaft rotatable responsive to movement of said mask from the open to the closed position, said cam means including a cam mounted on an end of said shaft.

9. The luminometer of claim 1 wherein said means for injecting a reagent includes at least one injector cannula in communication with a reservoir, pump means for dispensing a predetermined quantity of reagent from said reservoir through said cannula and means for advancing said cannula through the aperture in said mask and for retracting said cannula.

10. The luminometer of claim 9 wherein said means for advancing and retracting includes a biased piston surrounding a portion of said cannula and solenoid means surrounding said piston for advancing said piston and cannula when said solenoid is energized.

11. The luminometer of claim 10 further comprising piston bias means for retracting said piston and cannula when said solenoid is deenergized.

12. The luminometer of claim 11 wherein said piston is hollow and includes a removable end surrounding said cannula whereby when said end is removed from said piston said cannula can be withdrawn therefrom.

13. The luminometer of claim 12 wherein three injector cannulas are provided, each communicating with a separate reservoir.

14. The luminometer of claim 9 wherein said pump means includes a syringe pump containing said reservoir and an outlet, means for activating said syringe and conduit means connecting said outlet and said cannula for communication between said reservoir and cannula.

15. The luminometer of claim 14 wherein said means for activating includes a stepper motor having an outlet shaft, a pinion integral with said shaft, and a rack coupled to said pump and driven by rotation of said pinion.

16. The luminometer of claim 13 wherein said pump means comprises a separate syringe pump and reservoir for each injector cannula.

17. The luminometer of claim 16 where said means for actuating includes a separate stepper motor for each syringe pump.

* * * * *